United States Patent [19]
Dowgul

[11] 4,193,966
[45] Mar. 18, 1980

[54] CARBON DIOXIDE ABSORBENT CANNISTER WITH CONDENSATE CONTROL

[75] Inventor: Ronald W. Dowgul, Panama City Beach, Fla.

[73] Assignee: The United States of America as represented by the Secretary of the Navy, Washington, D.C.

[21] Appl. No.: 915,635

[22] Filed: Jun. 15, 1978

[51] Int. Cl.[2] ........................ B01J 7/02; A61M 15/00
[52] U.S. Cl. .................................... 422/122; 422/173; 422/177; 422/211; 128/205.28
[58] Field of Search ............... 422/177, 211, 175, 206, 422/205, 215, 120, 122, 173; 165/179; 128/142.7, 142 R, 142.2, 142.5, 191 R; 55/267, 387, 388, DIG. 33; 423/230

[56] References Cited

U.S. PATENT DOCUMENTS

| | | | |
|---|---|---|---|
| 2,608,968 | 9/1952 | Moseley | 165/179 |
| 2,731,709 | 1/1956 | Gaddis et al. | 165/179 |

FOREIGN PATENT DOCUMENTS

| | | | |
|---|---|---|---|
| 128606 | 8/1948 | Australia | 128/142 |
| 668081 | 8/1963 | Canada | 55/387 |
| 29162 | of 1912 | United Kingdom | 55/387 |
| 106695 | 6/1917 | United Kingdom | 128/191 R |

*Primary Examiner*—R. E. Serwin
*Assistant Examiner*—Chris Konkol
*Attorney, Agent, or Firm*—Richard S. Sciascia; Harvey A. David

[57] ABSTRACT

A carbon dioxide absorbent cannister in underwater breathing apparatus of the forced recirculation type. The cannister includes a plurality of stackable condenser elements that serve to cool exhaled gas of high relative humidity so that water, necessary to the desired carbon dioxide removing reaction, is condensed from the gas. The condenser elements are characterized by a plurality of radial, blade-like legs, the outer ends of which are in heat transfer relation to the cannister wall, and by a conical diffuser disc that serves as a heat sink.

8 Claims, 4 Drawing Figures

CARBON DIOXIDE ABSORBENT CANNISTER WITH CONDENSATE CONTROL

BACKGROUND OF THE INVENTION

This invention relates to underwater breathing apparatus of the type wherein breathing gas is circulated through a carbon dioxide absorbing cannister, and more particularly to an improved carbon dioxide absorbing cannister therefor.

There are numerous configurations of underwater breathing apparatus utilizing a carbon dioxide absorbing medium, such as a composition of sodium hydroxide or barium hydroxide, to remove carbon dioxide from the breathing gas so that it can be recirculated to the diver. In the case of mixed gas (usually helium and oxygen) diving to great depths, such recirculation is principally in the interest of economy and logistics relative to the acquisition and storage of large quantities of helium. A typical apparatus comprises a cannister or chamber in which a bed of particulate carbon dioxide absorbent material is confined, and through which the breathing gas is passed prior to recirculation to the diver. The motive power for accomplishing the recirculation is usually derived from make-up gas delivered at relatively high pressure to a nozzle that discharges into the throat of an ejector passage.

A major problem of long standing has been that of providing a carbon dioxide absorbing cannister, or scrubber, that will remain active and useful for the prolonged periods of time common to mixed gas dives. The mentioned compositions, as well as others, remove carbon dioxide through an exothermic reaction that requires the presence of water to proceed. Water in the absorbent material may be supplemented by the moisture in the exhaled breathing gas which often enters the cannister at, or close to, one hundred percent humidity, and substantially at ambient water temperature. Failure of the charge or bed of absorbent in the cannister to be effective through any period approaching its calculated effective life has generally been experienced and often provides the limiting factor to the length of a dive. Simply enlarging the absorbent bed has not helped to any useful degree, nor have various attempts at directing the gas flow to unused areas of the absorbent bed by baffling.

It is believed that such failures of the carbon dioxide absorbent cannisters are due to heating of the incoming air as a result of the exothermic reaction that occurs in a zone of the charge proximate to the inlet and extending for a portion of the length of the cannister. Although the incoming air is at or near one hundred percent relative humidity, as it passes into the mentioned zone it becomes heated, the relative humidity falls, and the air actually takes moisture from the remaining carbon dioxide absorbent charge. The remaining charge becomes drier and is unable to enter into the carbon dioxide absorbing reaction for lack of water.

SUMMARY OF THE INVENTION

With the foregoing in mind, it is a principal object of this invention to provide, in an underwater breathing apparatus, an improved carbon dioxide absorbent cannister or scrubber device.

Another object of this invention is to provide an improved carbon dioxide absorbing device, useful in recirculating mixed gas diving systems, that is characterized by an extended useful life of the absorbent charge, which useful life more nearly approaches the actual capacity of the charge than has generally been achieved heretofore.

Yet another object is the provision of an improved cannister construction that operates to avoid the drying out of large portions of a carbon dioxide absorbent bed or charge of the type characterized by an exothermic reaction requiring water.

Still another object is the provision of a cannister construction that is rugged in construction, reliable in use, and reasonably easy to fill with a particulate absorbent charge.

Other objects and many of the attendant advantages will be readily appreciated as the subject invention becomes better understood by reference to the following detailed description, when considered in conjunction with the accompanying drawings.

DESCRIPTION OF THE PREFERRED EMBODIMENT

Figure 1:
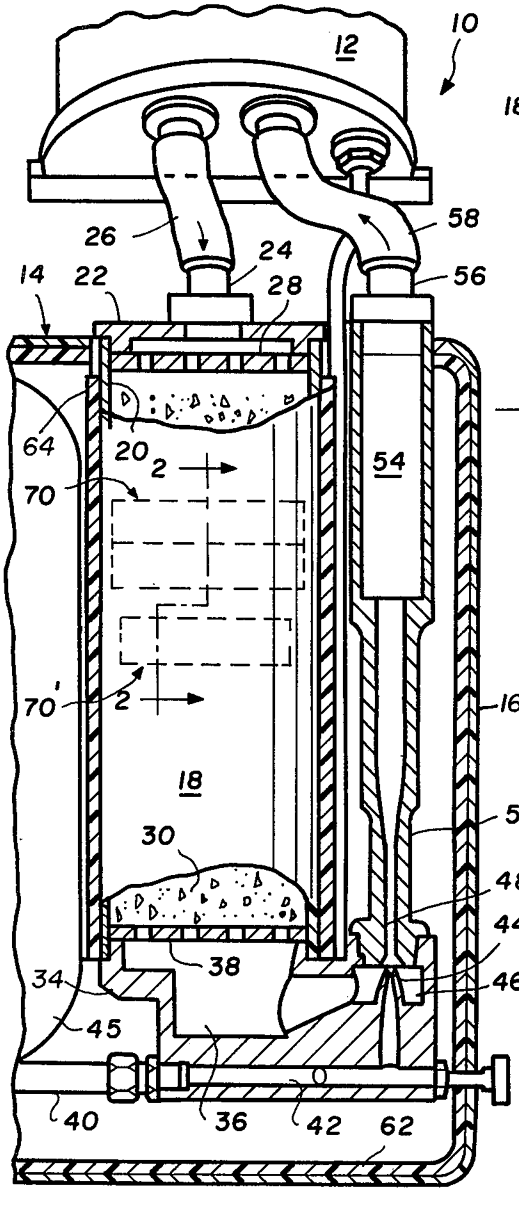
FIG. 1 is a fragmentary view, partly in section, of an underwater breathing apparatus including a carbon dioxide absorbing cannister embodying this invention.

Referring first to FIG. 1 of the drawings, an underwater breathing apparatus is indicated generally at 10 and is of a mixed gas, recirculating or rebreather type used for deep diving and in which the invention is used to advantage. The apparatus 10 includes a helmet 12 and a back-pack assembly 14 comprising a shell or housing 16 formed of light weight metal or plastic and containing a carbon dioxide absorbing cannister 18.

The cannister 18 comprises a hollow container in the form of a cylindrical wall 20, preferably formed of aluminum or other rigid material having good thermal conductivity. The upper end of the cannister 18 is provided with a closure member 22 having a connector 24 for coupling a flexible exhaust conduit or hose 26 leading from the helmet 12 to the cannister. The closure member 22 is provided with a screen or perforated plate 28 for confining a charge or bed 30 of particulate carbon dioxide absorbing material such as a composition of sodium hydroxide or barium hydroxide. Suitable compositions are well known in the art, being sold under a variety of trade means such as "SODASORB" by W. R. Grace & Co., Lexington, Massachusetts, or "BARALYME" by Chemitron, Medical Products Division, Stuyvesant Falls, New York, and are characterized by an exothermic reaction requiring water to proceed.

At its lower end, the cannister 18 is provided with an ejector or eductor pump means for drawing gas through the absorbent bed 30. This pump means comprises a metal body 34 having a cavity 36 and receiving the end of cylindrical wall 20. A screen or perforated plate 38, similar to plate 28, is carried by the body 34 for confining the absorbent bed above the cavity 36.

A makeup supply of breathing gas is introduced, via a pipe 40, into a passage 42 in the body 34 and which communicates with a metering eductor nozzle 44. This supply of gas may come either from a self-contained source, such as a bottle 45, or from an external source via an umbilical hose (not shown). The cavity 36 communicates, through a chamber 46 surrounding the nozzle 44, with the throat or passage of an ejector tube 50. The passage 48 opens into a chamber which contains a muffler 54 for attenuating the sounds of the ejector pump. A breathing gas heater may be incorporated in or replace the muffler 54 as necessary to the circumstances of use. A connector 56 couples the filter or heater chamber to a flexible, helmet supply hose 58.

It will be recognized that high pressure gas flowing through the nozzle 44 will effect a reduction in pressure in the cavity 36 that will draw exhaust gas from the helmet 12, through the hose 26 and the carbon dioxide absorbing cannister 18. The scrubbed gas exiting the cannister 18 is mixed with the make-up gas from nozzle 44 and returned to the helmet for rebreathing. Because of the extremely low temperatures usually encountered in deep diving, the interior of the shell 16, which in this example is free-flooding, may be provided with a thermally insulating lining 62. In addition, the cylindrical wall 20 of the cannister 18 may be sheathed with a thermally insulating jacket 64. Alternatively, the shell 16 may be flooded with a supply of heating water. Thus far, the construction and operation of the apparatus 18 is conventional.

In accordance with this invention, the cannister 18 is provided with moisture condensing means for effecting cooling of exhaust gas during its passage through the absorbent bed 30. A plurality of condenser elements 70 and 70' are shown in dotted lines in FIG. 1, and will be described in detail as this specification proceeds.

Figure 2:
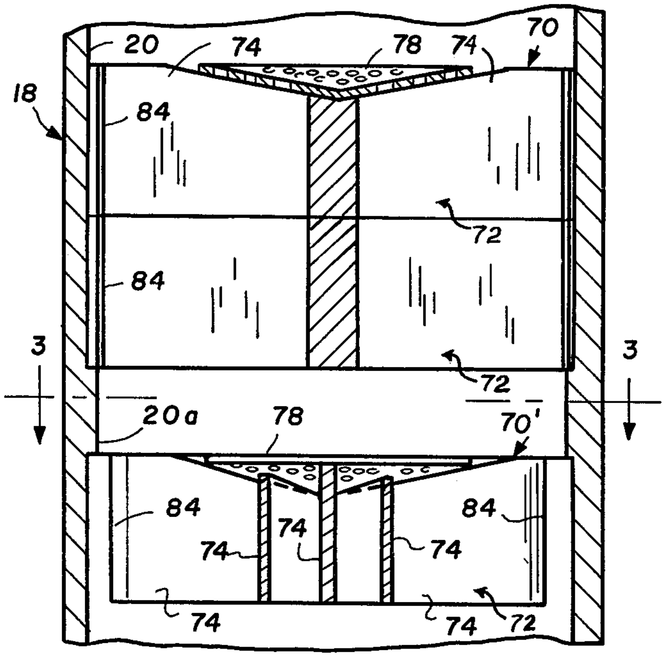
FIG. 2 is a vertical sectional view, on an enlarged scale, of a portion of the cannister of FIG. 1.
Figure 3:
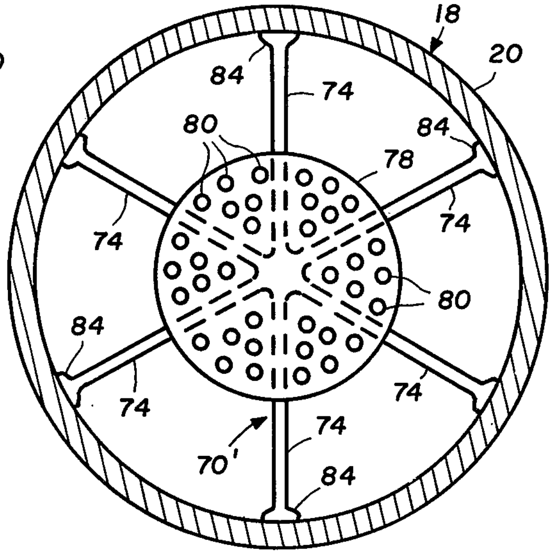
FIG. 3 is a sectional view taken substantially along line 3—3 of FIG. 2.

Referring now to FIGS. 2–3, in which the absorbent compound has been omitted for clarity, the condenser elements 70 and 70' are disposed in series within the cylindrical wall 20 of the cannister 18. In this example, the condenser element 70, which is longer than the element 70', is embedded in the upper regions of the bed of absorbent composition adjacent the inlet connection, while the element 70' is spaced downstream therefrom. This spacing is conveniently determined by a thickened wall portion or internal rib **20*a* of the wall 20**, presenting upper and lower shoulders against which the spaced elements are abutted.

Figure 4:
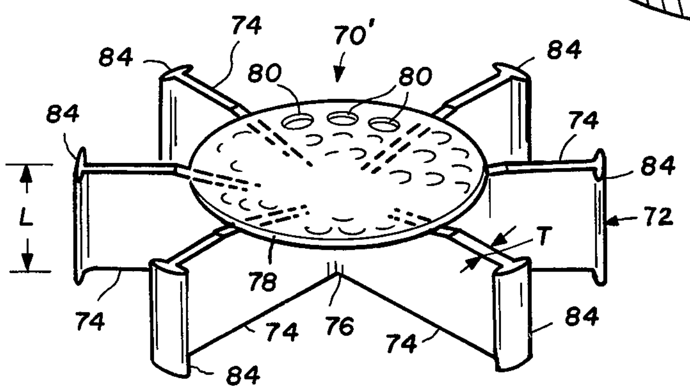
FIG. 4 is a perspective view of a condenser element of the cannister.

As is best illustrated in FIG. 4, the condenser element 70', which, except for its length, is substantially identical to element 70, is formed of a rigid material having good thermal conductivity such as aluminum or brass and comprises a plurality of radially extending, blade-like legs 74 that are joined at a common origin or center 76. In this example, the element 70' comprises a casting 72 including six such legs, each disposed at angles of 60° to the adjacent legs. The legs 74 have a length L, in the direction of gas flow, that is about one tenth the length of the cannister wall 20. Thus, for a cannister of say, 20 inches in length and 6 inches inside diameter, the length L of the element 70' is about 2 inches. The thickness T of each leg 74 is a small fraction of the length L thereof.

The upper edges of the legs 74 of the casting 72 are formed or machined to slope downwardly toward the center of the casting so as to accommodate a slightly conical, heat sink and gas diffuser disc 74 with its vertex pointing down. The disk 78, which forms a part of the condenser element 70', has a plurality of apertures 80 therethrough, and is brazed or welded to the legs 74 to assure good thermal transfer between the disc and legs. The disc 78 lies generally transverse to the flow of gas through the cannister and its diameter is about one-half the inside diameter of the cylindrical wall 20 so as to define a substantially annular space between the outer edge of the disc and the wall. The span of the element 70' is such as to permit a sliding fit within the cylindrical wall 20, and the outer ends of the legs 74 are provided with enlargements 84 presenting arcuate outer surfaces that are complimentary to the inner curvature of the wall and are adapted to fit snugly thereagainst.

The longer, upper condenser element 70 is conveniently constructed by welding two of the six legged castings 72 together in end to end stacked relation so as provide legs 74 having a length of 2 L, or about two tenths of the length of the cannister wall 20. The upper edges of these legs 74 are sloped downwardly and inwardly, as in the aforedescribed element 70', to accommodate a disc 78 forming part of the condenser element 70.

The condenser elements 70, 70' when assembled in the cylindrical wall 20 against opposite ends of the abutment rib **20*a* as mentioned earlier, are rotated 30° relative to one another so that the legs 74 of element 70 are staggered with respect to the legs 74 of element 70'. With the elements 70 and 70', so assembled, the enlargements 84 at the ends of the legs 74 thereof are welded or brazed to the inner surface of the wall 20 to assure that they will remain in position and also to assure good thermal conductivity between the legs 74** and that wall. Alternatively, the condenser elements may be made to have a shrink fit with the cannister wall.

It will be noted that the top end of the longer condenser element 70 is buried in the upper portion of the absorbent bed 30, and that the lower end of the element 70' is located at about the middle of the bed. Some variations in location, number, and lengths of condenser elements may, of course, be made to accommodate various operating conditions.

In operation, the metal wall and the condenser elements 70, 70' are cooled by ambient water. This is so, even if the wall is provided with an insulating sheath 64, due to a path of heat conductivity to the water through the closure member 22 and the body 34. Carbon dioxide in the moist or humid exhaust gas entering the bed 30 in the upper region of the cannister 18 commences the exothermic reaction by which the carbon dioxide is removed from the gas. The exothermic reaction tends to heat the upper portion of the bed and the gas, a factor which, if it were not for the condenser elements 70, 70' would cause the gas to actually remove moisture from the remaining portions of the bed 30 and inhibit continuance of the reaction therein.

The condenser elements, which are maintained cool relative to the temperature of the passing gas by the mentioned thermally conductive path, and particularly the diffuser discs 78, serve as heat sinks or cooling means for the passing gas. As the gas flows over, around, and through the condenser elements it is cooled or prevented from materially rising in temperature due to the exothermic reaction. The gas is thereby prevented from taking moisture out of the bed 30 of absorbent composition and inhibiting or stopping the carbon dioxide absorbing reaction. Accordingly, the reaction is enabled to continue through an increased portion of the absorbent composition. When the ambient temperatures are sufficiently low, the gas passing the condenser elements 70, 70' can be cooled below its dew point, in which case it necessarily gives up some moisture, as a condensate, to the bed 30. In either case, the invention controls the presence of moisture so as to maintain the carbon dioxide removal reaction substantially throughout the bed. The effective life of a charge or bed 30 is therefore materially extended. In actual practice, a cannister 18 containing about twelve pounds of absorbent compound, of the type mentioned, has provided a useful life in the range of about 8.5 to about 11 hours as compared to a useful life of about 3 hours for a cannister of conventional construction and a like amount of absorbent compound.

The conical shape of the discs 78 aids in ensuring that no voids will be left in the absorbent bed 30 when filling the cannister 18. This is an important feature in that such voids can lead to material reduction in the useful life of a cannister charge.

Obviously, other embodiments and modifications of the subject invention will readily come to the mind of one skilled in the art having the benefit of the teachings presented in the foregoing description and the drawing. It is, therefore, to be understood that this invention is not to be limited thereto and that said modifications and embodiments are intended to be included within the scope of the appended claims.

What is claimed is:

1. A cannister for use in an underwater breathing apparatus of the rebreather or recirculated breathing gas type and containing a bed of absorbing composition of the type characterized by an exothermic reaction requiring the presence of moisture, said cannister comprising:

a hollow container comprising a thermally conductive wall and adapted to contain said composition, said container comprising inlet means at one end for admitting carbon dioxide containing breathing gas at substantially 100% relative humidity, and outlet means at the opposite end for exiting breathing gas, after passage through said composition, from which said carbon dioxide has been removed;

said container having a predetermined length and including portions exposed during use to an ambient medium at temperatures substantially at the dew point of said breathing gas upon admission to said container;

condenser means, mounted in said container in contact with said composition, for conducting heat from said gas admission and while passing through said composition, whereby the moisture content of said composition is maintained so as to support said reaction through an extended period;

said condenser means comprising at least a first condenser element comprising a plurality of leg portions formed of a thermally conductive material and extending from a common origin within said container, each of said leg portions having an outer end in thermally conducting contact with the inner surface of said wall of said container, a heat sink and diffuser disc comprising a thermally conductive material and fixed to said leg portions, said disc lying generally transversely of the principal direction of flow through the cannister and defining a space between the outer edge of the disc and said wall, and said condenser element having a length in said principal direction of flow that is in the range of from about one-tenth to about two-tenths of said predetermined length of said cannister.

2. A cannister as defined in claim 1, and wherein:

said condenser means comprises a plurality of said condenser elements arranged in series along said principal direction of flow.

3. A cannister as defined in claim 2, and wherein:

said wall is cylindrical in configuration;

said leg portions of said condenser element extend at equal angles to one another; and said disc is provided with a plurality of apertures.

4. A cannister as defined in claim 3, and wherein:

each of said condenser elements comprises six of said leg portions each disposed at 60° to the adjacent leg portions of the same condenser element;

said leg portions having a thickness that is a small fraction of the length thereof in said principal flow direction;

the upper edges of said leg portions facing said flow being sloped downwardly toward said common origin;

each of said discs being conical in configuration and being disposed against said sloped edges with the vertex pointing downwardly in said direction of principal flow.

5. A cannister as defined in claim 4, and wherein:

a first of said condenser elements is embedded in said composition adjacent said inlet means; and a second of said condenser elements is embedded in said composition below said first of said condenser elements and in spaced relation thereto, said second of said condenser elements having its leg portions rotationally displaced from alignment with the leg portions of said first of said condenser elements.

6. A cannister as defined in claim 5, and wherein:

said first of said condenser elements is about twice the length of said second of said condenser elements.

7. A cannister as defined in claim 6, and wherein:

said outer ends of said leg portions are characterized, at least before being fixed to said wall, by enlargements presenting surfaces that are complementary to and engaging the inner surface of said wall.

8. A cannister as defined in claim 7, and wherein said container further comprises foraminous retainer means adjacent said inlet and outlet means for confining said bed of particulate composition.

* * * * *